(12) United States Patent
Valencia et al.

(10) Patent No.: US 8,038,692 B2
(45) Date of Patent: Oct. 18, 2011

(54) MODULAR DESIGN FOR OPHTHALMIC SURGICAL PROBE

(75) Inventors: Salomon Valencia, Aliso Viejo, CA (US); Jose Luis Lopez, Cypress, CA (US); Jack R. Auld, Laguna Niguel, CA (US)

(73) Assignee: Novartis AG, Basel (CH)

( * ) Notice: Subject to any disclaimer, the term of this patent is extended or adjusted under 35 U.S.C. 154(b) by 385 days.

(21) Appl. No.: 11/554,812

(22) Filed: Oct. 31, 2006

(65) Prior Publication Data

US 2008/0172077 A1    Jul. 17, 2008

(51) Int. Cl.
 A61F 9/00    (2006.01)
 A61F 9/007    (2006.01)

(52) U.S. Cl. .................................. 606/166; 606/171

(58) Field of Classification Search .......... 606/166–171, 606/107; 600/562, 564, 568; 604/22
See application file for complete search history.

(56) References Cited

U.S. PATENT DOCUMENTS

| | | | |
|---|---|---|---|
| 3,884,238 A | 5/1975 | O'Malley et al. | |
| 4,493,698 A | 1/1985 | Wang et al. | |
| 4,577,629 A * | 3/1986 | Martinez | 606/171 |
| 4,696,298 A | 9/1987 | Higgins et al. | |
| 4,757,814 A | 7/1988 | Wang et al. | |
| 4,819,635 A | 4/1989 | Shapiro | |
| 4,841,984 A | 6/1989 | Armeniades et al. | |
| 4,909,249 A | 3/1990 | Akkas et al. | |
| 4,940,468 A | 7/1990 | Petillo | |
| 4,986,827 A | 1/1991 | Akkas et al. | |
| 5,019,035 A * | 5/1991 | Missirlian et al. | 604/22 |
| 5,020,535 A | 6/1991 | Parker et al. | |
| 5,024,652 A | 6/1991 | Dumenek et al. | |
| 5,047,008 A * | 9/1991 | de Juan et al. | 604/22 |
| 5,059,204 A | 10/1991 | Lawson et al. | |
| 5,061,238 A | 10/1991 | Shuler | |
| 5,176,628 A | 1/1993 | Charles et al. | |
| 5,284,472 A | 2/1994 | Sussman et al. | |
| 5,354,268 A | 10/1994 | Peterson et al. | |
| 5,380,280 A | 1/1995 | Peterson | |
| 5,423,844 A | 6/1995 | Miller | |
| 5,474,532 A | 12/1995 | Steppe | |
| 5,520,652 A | 5/1996 | Peterson | |
| 5,630,827 A | 5/1997 | Vijfvinkel | |
| 5,674,194 A | 10/1997 | Jung et al. | |
| 5,733,297 A | 3/1998 | Wang | |
| 5,782,849 A | 7/1998 | Miller | |
| 5,833,643 A | 11/1998 | Ross et al. | |
| 5,976,121 A | 11/1999 | Matern et al. | |
| 6,010,496 A | 1/2000 | Appelbaum et al. | |
| 6,488,695 B1 | 12/2002 | Hickingbotham | |
| 6,514,268 B2 | 2/2003 | Finlay et al. | |
| 6,575,990 B1 | 6/2003 | Wang et al. | |
| 6,758,824 B1 * | 7/2004 | Miller et al. | 600/568 |
| 6,773,445 B2 | 8/2004 | Finlay et al. | |
| 2002/0161398 A1 | 10/2002 | Hickingbotham | |
| 2003/0078609 A1 | 4/2003 | Finlay et al. | |
| 2005/0156387 A1 | 7/2005 | Chen et al. | |
| 2006/0271082 A1 * | 11/2006 | Kirchhevel et al. | 606/170 |

FOREIGN PATENT DOCUMENTS

EP    0442851 A    8/1991

* cited by examiner

Primary Examiner — Amy Lang
(74) Attorney, Agent, or Firm — W. David Lee

(57) ABSTRACT

An ophthalmic surgical probe having a modular drive assembly and a skin that is removable from the drive assembly. This design simplifies probe manufacturing and provides greater manufacturing flexibility.

5 Claims, 2 Drawing Sheets

MODULAR DESIGN FOR OPHTHALMIC SURGICAL PROBE

FIELD OF THE INVENTION

The present invention generally pertains to microsurgical instruments. More particularly, but not by way of limitation, the present invention pertains to microsurgical instruments used in posterior segment ophthalmic surgery, such as vitrectomy probes.

DESCRIPTION OF THE RELATED ART

Many microsurgical procedures require precision cutting and/or removal of various body tissues. For example, certain ophthalmic surgical procedures require the cutting and/or removal of the vitreous humor, a transparent jelly-like material that fills the posterior segment of the eye. The vitreous humor, or vitreous, is composed of numerous microscopic fibers that are often attached to the retina. Therefore, cutting and removal of the vitreous must be done with great care to avoid traction on the retina, the separation of the retina from the choroid, a retinal tear, or, in the worst case, cutting and removal of the retina itself.

The use of microsurgical cutting probes in posterior segment ophthalmic surgery is well known. Such vitrectomy probes are typically inserted via an incision in the sclera near the pars plana. The surgeon may also insert other microsurgical instruments such as a fiber optic illuminator, an infusion cannula, or an aspiration probe during the posterior segment surgery. The surgeon performs the procedure while viewing the eye under a microscope.

Conventional vitrectomy probes typically include a hollow outer cutting member, a hollow inner cutting member arranged coaxially with and movably disposed within the hollow outer cutting member, and a port extending radially through the outer cutting member near the distal end thereof. Vitreous humor is aspirated into the open port, and the inner member is actuated, closing the port. Upon the closing of the port, cutting surfaces on both the inner and outer cutting members cooperate to cut the vitreous, and the cut vitreous is then aspirated away through the inner cutting member. U.S. Pat. Nos. 4,577,629 (Martinex); 5,019,035 (Missirlian et al.); 4,909,249 (Akkas et al.); 5,176,628 (Charles et al.); 5,047,008 (de Juan et al.); 4,696,298 (Higgins et al.); and 5,733,297 (Wang) all disclose various types of vitrectomy probes, and each of these patents is incorporated herein in its entirety by reference.

Conventional vitrectomy probes include "guillotine style" probes and rotational probes. A guillotine style probe has an inner cutting member that reciprocates along its longitudinal axis. A rotational probe has an inner cutting member that rotates about is longitudinal axis. In both types of probes, the inner cutting members are actuated using various methods. For example, the inner cutting member can be moved from the open port position to the closed port position by pneumatic pressure against a piston or diaphragm assembly that overcomes a mechanical spring. Upon removal of the pneumatic pressure, the spring returns the inner cutting member from the closed port position to the open port position. As another example, the inner cutting member can be moved from the open port position to the closed port position using a first source of pneumatic pressure, and then can be moved from the closed position to the open port position using a second source of pneumatic pressure. As a further example, the inner cutting member can be electromechanically actuated between the open and closed port positions using a conventional rotating electric motor or a solenoid. U.S. Pat. No. 4,577,629 provides an example of a guillotine style, pneumatic piston/mechanical spring actuated probe. U.S. Pat. Nos. 4,909,249 and 5,019,035 disclose guillotine style, pneumatic diaphragm/mechanical spring actuated probes. U.S. Pat. No. 5,176,628 shows a rotational dual pneumatic drive probe.

In many conventional vitrectomy probes, the engine and the shell or skin are tied together to yield a functional probe. A disadvantage to this is that the skin serves as both an ergonomic component as well as a part that is responsible for function. Changing between different probe types (i.e. 20, 23, 25 gage probes) requires that the internal features of the skin be changed to accommodate the corresponding functional interfaces such as seal design and tip geometry. This results in less flexibility.

Therefore, a need exists for an improved vitrectomy probe that exhibits more flexibility. Such flexibility should enable future design and manufacturing flexibility, utilize a number of common components in overall probe design, and be able to convert to multiple gage size probes using the same engine parts.

SUMMARY OF THE INVENTION

The present invention is an ophthalmic surgical having a skin removably coupled to an engine, a needle holder, a needle, and a cutter. The engine has a drive shaft support member and a drive shaft extending axially from the engine. The needle holder has a bushing disposed therein and an opening for removably engaging the drive shaft support member. The needle has a first coupling rigidly coupled thereto. The first coupling is for removably engaging the bushing. The cutter has a second coupling rigidly coupled thereto. The cutter is slidably disposed within the needle, and the second coupling is for removably engaging the drive shaft.

BRIEF DESCRIPTION OF THE DRAWINGS

For a more complete understanding of the present invention, and for further objects and advantages thereof, reference is made to the following description taken in conjunction with the accompanying drawings, in which.

DETAILED DESCRIPTION OF THE PREFERRED EMBODIMENTS

Figure 1:
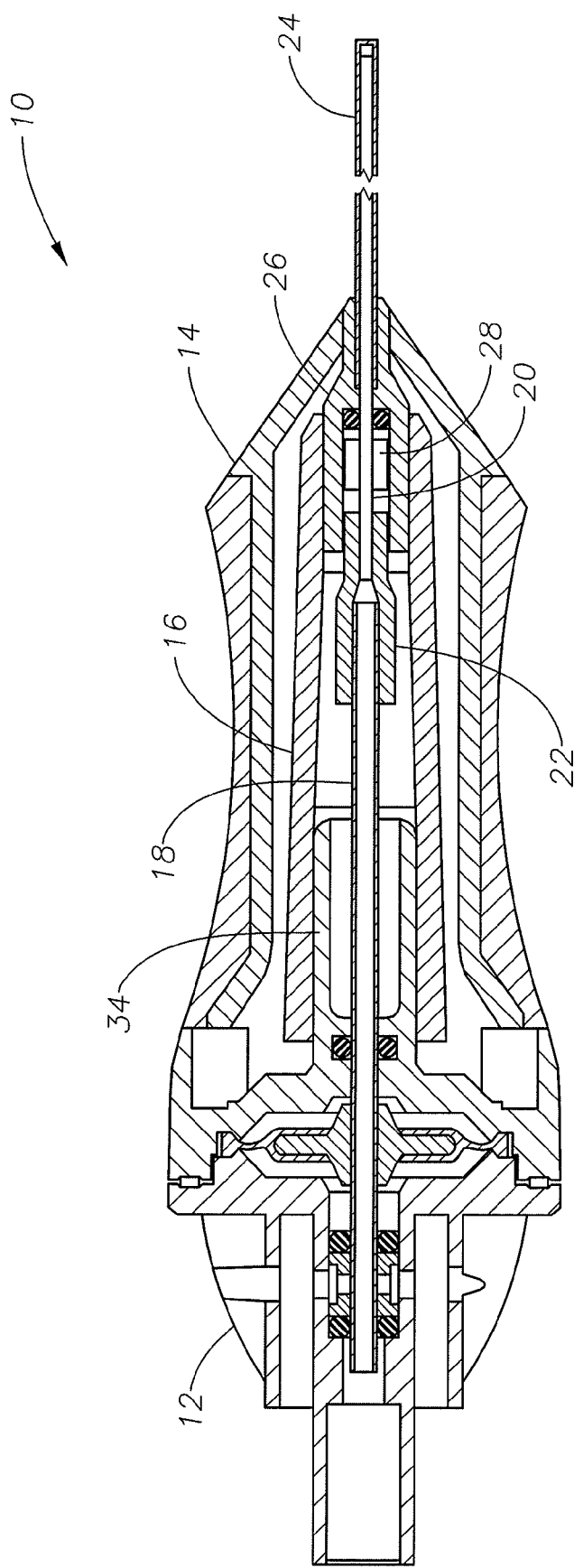
FIG. 1 is a sectional view of the ophthalmic surgical probe of the present invention.
Figure 2:
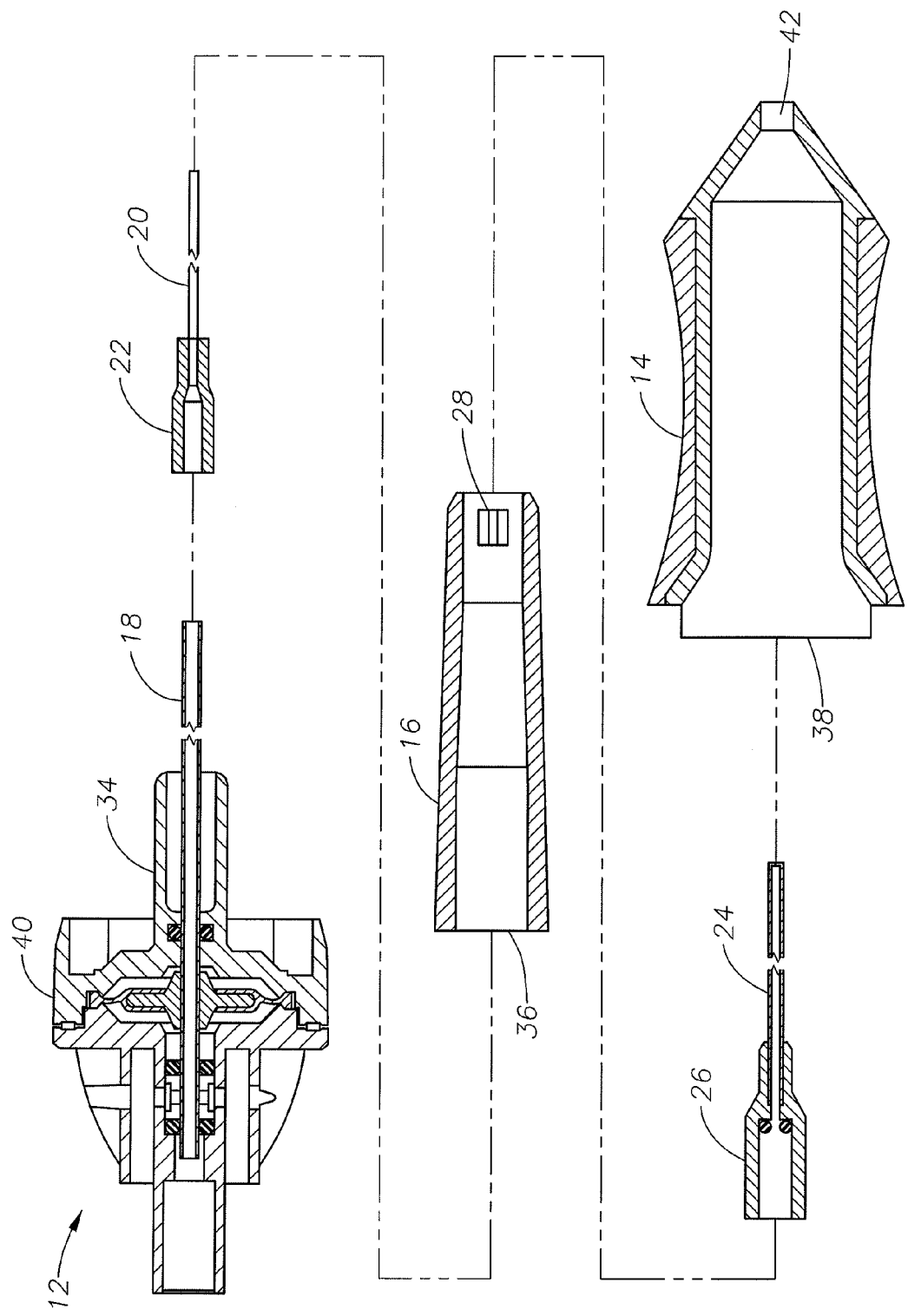
FIG. 2 is an exploded, sectional view of the ophthalmic surgical probe of FIG. 1.

The preferred embodiments of the present invention and their advantages are best understood by referring to FIGS. 1-2 of the drawings, like numerals being used for like and corresponding parts of the various drawings.

Vitrectomy probe 10 consists of engine 12, shell or skin 14, needle holder 16, drive shaft 18, cutter 20, and needle 24. Although the ophthalmic surgical probe of the present invention is described herein in connection with a vitrectomy probe 10, the present invention is applicable to other ophthalmic or other surgical probes, instruments, and handpieces. Cutter coupling 22 is integrally formed on the proximal end of cutter 20. Needle coupling 26 is integrally formed on the proximal end of needle 24. Drive shaft 18 extends axially from engine 12. Distal end of drive shaft 18 removably engages cutter coupling 22 of cutter 20. Drive shaft support member 34 removably engages opening 36 of needle holder 16. Drive shaft support member 34, drive shaft 18, and cutter coupling 22 are disposed within needle holder 16. Bushing 28 within needle holder 16 removably engages needle coupling 26 of needle 24, such that cutter 20 is slidably disposed within needle 24. Needle coupling 26, needle holder 16, cutter coupling 22, drive shaft 18, and drive shaft support member 34 are disposed entirely within skin 14. Skin 14 contains opening 38 which removably engages body 40 of engine 12. Needle 24 extends through opening 42 in skin 14.

Engine 12 may be any type of engine suitable for driving vitrectomy probe 10, but is most preferably a pneumatic engine or an electric engine. Drive shaft 18 may be made of any suitable material, but is most preferably stainless steel. Needle 24 and cutter 20 may be made of any material suitable for posterior segment ophthalmic surgery, but are most preferably made from surgical stainless steel. Skin 14, needle coupling 26, and cutter coupling 22 are most preferably made from a lightweight material such as aluminum or rigid plastic.

During manufacturing assembly, the modular design of probe 10 allows a worker to quickly and easily switch between building probes of various needle gages, such as a probe 10 with a 20 gage needle 24, a 23 gage needle 24, or a 25 gage needle 24. More specifically, the ability to quickly attach and remove skin 14 from body 40 of engine 12, to quickly couple different gages of needle 24 with needle holder 16 and cutter 20 via needle coupling 26 and bushing 28, and to quickly couple cutter 20 to drive shaft 18 via cutter coupling 22 greatly increases manufacturing flexibility and simplifies the assembly process of probe 10.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. An ophthalmic surgical probe with a modular construction, comprising:
   a skin having a distal opening and a proximal opening;
   an engine having a body, and a drive shaft support member and a drive shaft extending axially away from said engine;
   a needle holder having a bushing disposed therein and a proximal opening for removably engaging said drive shaft support member;
   a needle having a needle coupling rigidly coupled thereto, said needle coupling removably engaging said bushing; and
   a cutter having a cutter coupling rigidly coupled thereto, said cutter being slidably disposed within said needle, and said cutter coupling removably engaging said drive shaft;
   whereby:
      said drive shaft support member, said drive shaft, and said cutter coupling are operably disposed within said needle holder;
      said needle holder is received through said proximal opening of said skin so that said drive shaft support member, said needle holder, and said cutter coupling are disposed entirely within said skin;
      said needle extends through said distal opening of said skin; and
      said skin is removably engaged to said body of said engine.

2. The ophthalmic surgical probe of claim 1 wherein said engine comprises a pneumatic engine.

3. The ophthalmic surgical probe of claim 1 wherein said engine comprises an electric engine.

4. The ophthalmic surgical probe of claim 1 wherein said probe is a vitrectomy probe.

5. The ophthalmic surgical probe of claim 1 whereby said probe facilitates changing to different gages of said needle during manufacturing of said probe.

* * * * *